United States Patent [19]

Yoon et al.

[11] Patent Number: 4,981,149
[45] Date of Patent: Jan. 1, 1991

[54] METHOD FOR SUTURING WITH A BIOABSORBABLE NEEDLE

[75] Inventors: InBae Yoon, 2101 Highland Ridge Dr., Phoenix, Md. 21131; Samuel C. Yoon, Phoenix, Md.

[73] Assignee: InBae Yoon, Phoenix, Md.

[21] Appl. No.: 534,495

[22] Filed: Jun. 7, 1990

Related U.S. Application Data

[62] Division of Ser. No. 353,913, May 16, 1989, Pat. No. 4,932,962.

[51] Int. Cl.$^5$ ............................................. A61B 17/00
[52] U.S. Cl. ..................................... 128/898; 606/224; 606/227
[58] Field of Search .................. 128/898; 606/224–227

[56] References Cited

U.S. PATENT DOCUMENTS 4,936,835 6/1990 Haaga ................................. 604/265

Primary Examiner—Randall L. Green
Assistant Examiner—Gary Jackson
Attorney, Agent, or Firm—Epstein, Edell & Retzer

[57] ABSTRACT

Suture devices, primarily for use in endoscopic surgery, include a suture needle made of bioabsorbable material for pulling a length of suture material through bodily tissue allowing the suture needle to be inadvertently or intentionally left in the tissue, and a suture needle having a length of suture material attached thereto with a contractible loop or passage at the proximal end of the suture material to allow the suture needle to be passed therethrough, the loop or passage contracting to clamp or grip the suture material to function similar to a conventional tied suture knot.

2 Claims, 1 Drawing Sheet

U.S. Patent	Jan. 1, 1991	4,981,149
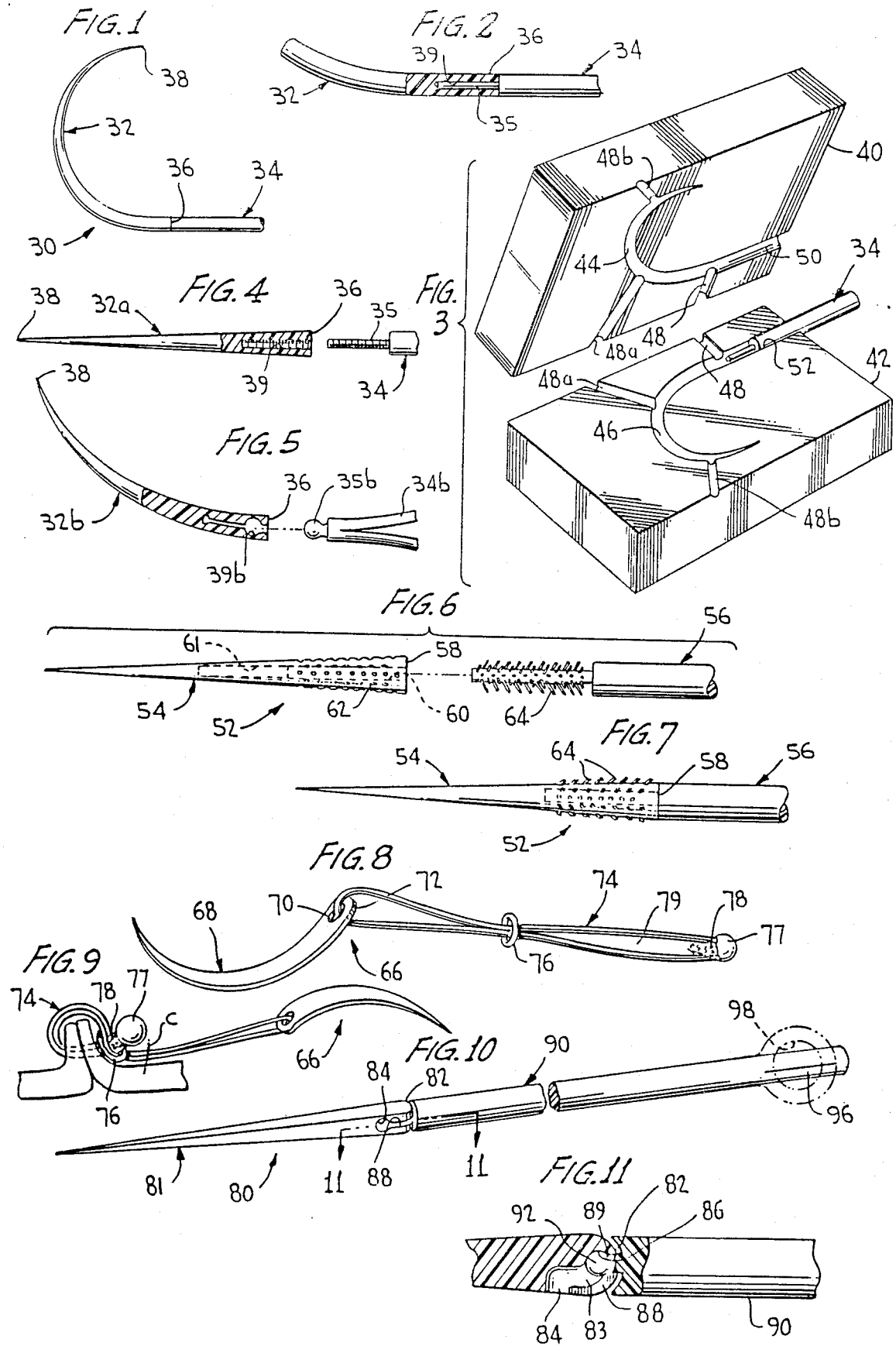

METHOD FOR SUTURING WITH A BIOABSORBABLE NEEDLE

This is a divisional application of application Ser. No. 07/353,913, filed May 16, 1989, Pat. No. 4,932,962.

BACKGROUND OF THE INVENTION

FIELD OF THE INVENTION

The present invention relates to surgical suture devices and, more particularly, to suture devices made of bioabsorbable materials particularly useful in endoscopic surgery and methods of suturing using such suture devices.

DISCUSSION OF THE PRIOR ART

Suturing of bodily tissue is a time consuming part of most surgical procedures including both open surgery and endoscopic or closed surgery. By open surgery is meant surgery wherein the surgeon gains access to the surgical site via a relatively large incision, and by endoscopic surgery is meant surgery wherein the surgeon gains access to the surgical site via one or more portals through which endoscopes are introduced to view the surgical site and through which instruments, such as forceps, cutters, applicators and the like, are introduced to the surgical site. There are many common endoscopic surgical procedures, including arthroscopy, laparascopy (pelviscopy), gastroentroscopy and laryngobronchoscopy, for example. In the past, suturing has been accomplished with the use of a sharp metal suture needle attached to the end of a length of suture material, the suture needle being caused to penetrate and pass through the tissue pulling the suture material through the tissue. Once the suture material has been pulled through the tissue, the surgeon ties a knot in the suture material, the knotting procedure allowing the surgeon to adjust the tension on the suture material to accommodate the particular tissue being sutured and control approximation, occlusion, attachment or other conditions of the tissue. The ability to control tension is extremely important to the surgeon regardless of the type of surgical procedure being performed; however, knotting of the suture material is time consuming and tedious work, particularly in microsurgery and endoscopic surgery. That is, in microsurgery suturing is necessarily time consuming due to the small size of the suture needle and the suture material and the concomitant difficult manipulation required to pass the suture needle through the tissue and to tie a knot in the suture material. With respect to endoscopic surgery, suturing and tying knots represents an even more time consuming procedure due to the difficult maneuvers required. Accordingly, while endoscopic surgery would be preferred for most procedures, the advantages are often outweighed by the disadvantages caused by the length of time required to complete the endoscopic surgical procedure, which time is greatly extended due to the time required for suturing. Another disadvantage of suturing with a metal suture needle and suture material during endoscopic surgery is that the suture needle is difficult to hold and manipulate and can be easily dropped. Should the suture needle be dropped, open surgery with its attendant disadvantages must be performed to find and remove the needle.

There have been many attempts to provide devices to take the place of conventional suturing with a suture needle and a length of suture material; however, such prior art devices have essentially been staples, clips, clamps or other fasteners not providing the adjustable tension obtained by the surgeon while knotting a length of suture material U.S. Pat. No. 3,827,277 to Weston, No. 4,060,089 to Noiles, No. 4,490,326 to Beroff et al, No. 4,513,746 to Aranyi et al, No. 4,532,926 to O'Holla, No. 4,548,202 to Duncan, No. 4,573,469 to Golden, et al No. 4,590,937 to Deniega, No. 4,595,007 to Mericle, No. 4,602,634 to Barkley, No. 4,646,741 to Smith, No. 4,671,280 to Dorband et al, No. 4,719,917 to Barrows et al and No. 4,741,337 to Smith et al are representative of such prior art devices for use in place of conventional suturing. Many of these prior art devices are made of bioabsorbable materials such that the devices are absorbed over time into the bodily tissue and do not have to be removed after the bodily tissue has healed.

There exist many compositions useful as bioabsorbable materials, as represented by the above patents and by U.S. Pat. No., 3,739,773 to Schmitt et al, No. 3,797,499 to Schneider, No. 4,141,087 to Shalaby et al, No. 4,300,565, to Rosensaft et al No. 4,523,591 to Kaplan et al and No. 4,649,921 to Koelmel et al which discuss characteristics of various bioabsorbable materials and medical devices desirably manufactured of such materials, such medical devices being of a type designed to be engaged in, embedded in or otherwise attached to various types of bodily tissue, such as bone, muscle, organs, skin and other soft tissue, to remain in place in the tissue until the device is absorbed into the body.

U.S. Pat. No. 3,570,497 to Lemole discloses a suture device formed of a needle with a piercing point extending from a latch cord carrying notches designed to pass through a latch collar, the latch cord being resilient to be curved upon itself to form a suture stitch without requiring tying of a knot; however, the latching function does not provide the same feel and tension control as knotting a length of suture material U.S. Pat. 4,548,202 to Duncan uses similar structure in a tissue fastener device in that serrations or angled barbs are provided on spaced legs passing through tissue to be engaged by an apertured receiver or a flexible filament mesh. U.S. Pat. No. 3,123,077 to Alcamo discloses a surgical suture carrying raised projections or depressions or teeth such as barbs or spicules to snag or penetrate tissue to effectively hold a sewed incision or wound.

Endoscopic surgery is preferred over open surgery due to the greatly reduced trauma and wound healing time for the patient and due to concomitant cost savings associated with shorter hospital stays and performing surgery without general anesthesia and in non-hospital or out-patient surgery sites Accordingly, there has been much effort spent to develop techniques for facilitating the suturing normally performed by use of a metal suture needle and a length of suture material. Alternative techniques proposed have included electrical coagulation, mechanical devices such as clips, clamps and staples, and lasers; however, no well accepted alternative has yet been found in that suturing and tying are essential and vital parts of most surgical procedures. That is, to date the proposed alternatives have had disadvantages, including increased risk to the patient, while not providing the surgeon with the advantages of suturing and tying and not being useful in a wide range of procedures to allow expansion of the areas in which endoscopic surgery can be effectively performed. Thus, there is a great need for suture devices, particularly useful in endoscopic surgery, that allow surgeons to suture and tie knots in a manner with which they are familiar without undue concern as to the loss of the suture needle and further for suture devices that allow controlled approximation of tissue and tying to produce controlled tension.

SUMMARY OF THE INVENTION

Accordingly, it is a primary object of the present invention to provide suture devices particulary useful in endoscopic surgery overcoming the above mentioned disadvantages of the prior art.

Another object of the present invention is to construct a suture needle of the type attached to a length of suture material to pull the suture material through tissue to be sutured of a bioabsorbable material such that, should the suture needle be dropped or lost during endoscopic surgery, open surgery is not required to remove the needle.

A further object of the present invention is to facilitate attachment of a length of suture material to a suture needle made of bioabsorbable material by using the plastic characteristics of the bioabsorbable material.

An additional object of the present invention is to form a loop or passage in the proximal portion of a length of suture material in a manner such that the loop or passage tightly grips the length of suture material after a suture needle attached to the distal end of the length of suture material has passed through the loop or passage to pull the length of suture material therethrough forming an adjustably controlled knot after suturing.

The present invention has another object in that a suture needle is formed of bioabsorbable material with a rigid distal portion having a sharp tip and semi-rigid or flexible proximal and/or central portions to facilitate manipulation of the suture needle for various procedures.

Yet an additional object of the present invention is to provide a suture needle that can be used to position a length of suture material in tissue to be sutured and can be left embedded in the tissue by constructing the suture needle of bioabsorbable material.

The present invention is generally characterized in a suture device for joining bodily tissue formed of a length of suture material and a suture needle having a distal end with a sharp penetrating point and a proximal end with means for engaging the length of suture material such that the suture needle can penetrate tissue to be sutured to pull the length of suture material through the tissue to leave the length of suture material in the tissue, the suture needle being made of bioabsorbable material whreby said suture needle can be absorbed by the body.

The present invention is further generally characterized in a method of sutureing bodily tissue during endoscopic surgery comprising the steps of suturing the bodily tissue with a suture needle made of bioabsorbable material and a length of suture material attached thereto and leaving the suture needle in the body to be absorbed thereby.

Some of the advantages of the present invention over the prior art are that open surgery is not required should a suture needle be dropped or lost during endoscopic surgery, suture needles can be made with controlled rigidity to facilitate specific surgical procedures, attachment of the suture needle to a length of suture material is facilitated by the plastic characteristics of the bioabsorbable material, and a knotting or suture tying function is provided by passing a suture needle through a contractible passage or loop carried at a proximal portion of a length of suture material attached to the suture needle.

Other objects and advantages of the present invention will become apparent from the following description of the preferred embodiments taken in conjunction with the accompanying drawings.

BRIEF DESCRIPTION OF THE DRAWINGS

FIG. 1 is a side view of a suture device formed of a suture needle and a length of suture material in accordance with the present invention.

FIG. 2 is a broken sectional view of the suture device of FIG. 1.

FIG. 3 is an exploded perspective view showing formation of the suture device of FIG. 1.

FIGS. 4 and 5 are broken sectional views of modifications of the suture device of FIG. 1.

FIG. 6 is an exploded side view of another embodiment of a suture device according to the present invention.

FIG. 7 is a side view of the assembled suture device of FIG. 6.

FIG. 8 is a perspective view of another embodiment of a suture device according to the present invention.

FIG. 9 is a broken side view illustrating use of the suture device of FIG. 8.

FIG. 10 is a perspective view of another embodiment of a suture device according to the present invention.

FIG. 11 is a section taken along line 11—11 of FIG. 10.

DESCRIPTION OF THE PREFERRED EMBODIMENTS

A suture device 30 according to the present invention is illustrated in FIGS. 1 and 2 and is formed of a suture needle 32 having a curved, C-configuration as shown in FIG. 1 or straight or slightly curved shapes as shown in FIGS. 4 and 5 at 32a and 32b, respectively, or any other conventional suture needle shape, the suture device 30 also including a length of suture material 34 attached or secured to a proximal end 36 of the suture needle. By suture needle is meant a needle specifically designed for penetrating bodily tissue and pulling through the tissue a length of suture material to approximate edges of tissue, such as result from an incision or wound, to permit the tissue to join together during healing Suture needles are severed from the suture material once the suturing procedure of placing sufficient stitches or loops of suture material in the tissue is completed and are commonly made of metal. That is, suture needles are not designed to remain in the tissue but rather serve only the purpose of penetrating the tissue to position the suture material therein. After the suturing procedure and severing of the suture needles, the suture needles are conventionally sterilized for reuse or, more commonly, discarded.

In accordance with the present invention, the suture needle 32 is made of bioabsorbable material even though suture needles are not intended to remain in the tissue as are medical devices commonly made of bioabsorbable material. The bioabsorbable material is rigid at a sharp point 38 on a distal portion of the suture needle to easily penetrate tissue to be sutured and can be rigid throughout the length thereof, or a proximal portion adjacent proximal end 36 can also be rigid while a central portion extending between the distal and proximal portions can be flexible to facilitate particular suturing maneuvers. In addition, both the central and proximal portions can be flexible for use in other suturing maneuvers, it being appreciated that the ability to make certain portions of the needle flexible provides many advantages in endoscopic surgery due to the limitations concomitant with suturing in a confined area with the use of a needle holder. The length of suture material 34 is preferably also made of bioabsorbable material but could be made of conventional materials, the suture material being flexible to conform to the desired suturing configuration in the tissue. For some uses, it is preferable for the suture material to be made of a flexible, elastic (stretchable) bioabsorbable material. The suture material 34 preferably has a diameter the same as the width or diameter of the proximal end 36 of the suture needle and has an end 35 extending from a distal portion and having a reduced diameter to be received in the bore 39 in a manner to produce a smooth profile to facilitate suturing. As shown in FIG. 3, a preferred manner of forming the suture device 30 is by molding the suture needle 32 with the end of the suture material 34 positioned in the mold such that the suture needle is formed simultaneously with attachment of the suture material. The mold has two parts 40 and 42 with recesses 44 and 46 therein having the shape of suture needle 32, and an inlet channel 48 is provided for injection of a bioabsorbable material under pressure. Channels 50 and 52 are formed in mold parts 40 and 42 to accommodate suture material 34 and are essentially extensions of recesses 44 and 46 such that, during injection molding of the suture needle 32, the end of the suture material 34 is captured and securely attached to the proximal end 36 of the suture needle. The end of the suture material can extend as far into the molding recesses as required to produce a secure attachment. In forming the suture needle 32, the plastic characteristics of the bioabsorbable material can be used to great advantage by controlling the flexibility or rigidity of the suture needle to facilitate use in particular surgical procedures. To this end, channels 48a and 48b can be positioned in mold parts 40 and 42 such that bioabsorbable materials with varying characteristics can be injected to create a suture needle having a specifically designed flexibility profile. For example, the portion adjacent sharp needle point 38 is preferably rigid, that is the portion distally of channel 48b, while a central portion between channels 48a and 48b can be flexible or rigid while the proximal portion between channels 48a and 48 can be flexible or rigid.

While it is preferred to mold the suture needle simultaneously with attaching the suture material since manufacture of the suture device is facilitated and made less expensive by accomplishing two manufacturing processes in a single step, the end of the suture material can also be attached to the proximal end 36 by various mechanical means such as by threading the bore 39a and the end 35a, as shown in FIG. 4, or providing a spherical recess 39b in proximal end 36b which is slit to expand to receive a ball-shaped end 35b on suture material 34b having two lengths as shown in FIG. 5. Additionally, the end of the suture material can be secured to the suture needle with the use of adhesives and/or heat treating or ultrasonic welding. Since the suture needle is made of bioabsorbable material, bore 39 can have any length desired thereby allowing more secure attachment of the suture material thereto. The suture material could also be secured in the bore of the suture needle by anchoring or staking; however, it is preferable to take advantage of the plastic characteristics of the bioabsorbable material of the suture needle as well as the plastic characteristics of the suture material, when made of bioabsorbable material, in that the end of the suture material can be formed in any suitable manner with protrusions to be received in the bore or recess in the proximal end of the suture needle with the latter having a configuration to lock the end therein.

The suture device 30 is used in a manner similar to conventional suturing, it being appreciated that, when used in endoscopic procedures, the suture needle 32 will be held by a conventional needle holder to cause the suture needle to penetrate through the tissue in a manner to thread the suture material in the tissue to approximate the edges of the tissue as desired. The suture needle 32 is severed from the suture material 34 after the suturing procedure is completed; and, should the suture needle be dropped and lost prior to removal through the portal, open surgery is not required to find and remove the suture needle since it is made of bioabsorbable material and can be absorbed by the body. Accordingly, the suture needle 32 can be left in the body after suturing due to inadvertence. Furthermore, since the suture needle is made of bioabsorbable material, the suture needle can be intentionally lodged in the tissue after suturing to additionally approximate and hold the tissue together. Accordingly, by making the suture needle of bioabsorbable material many unexpected advantages are obtained including facilitating manufacture of the suture needle to particular specifications as to rigidity and configuration, facilitating attachment of a length of suture material thereto, allowing endoscopic procedures to be performed with less apprehension relating to inadvertent loss of the suture needle and allowing the suture needle to be used to additionally secure the tissue.

Another embodiment of a suture device according to the present invention is illustrated in FIGS. 6 and 7 wherein a suture device 52 is formed of a suture needle 54 and a length of suture material 56 preferably made of flexible bioabsorbable material. The suture needle 54 is formed of bioabsorbable material to have a desired rigidity therealong as described above; and, while a straight configuration is illustrated, the suture needle can have any desired configuration corresponding to commonly used suture needles such as the configurations shown in FIGS. 1, 4 and 5. The suture needle 54 has a hollow proximal end 58 forming a bore or recess 60 therein, and angled perforations or holes 62 extend through the wall surrounding the bore. The end of the suture material 56 has angled, whisker-like filaments 64 extending rearwardly therefrom having a size to be received in the holes 62 in the suture needle, the holes 62 similarly extending rearwardly from the inner surface to the outer surface toward the proximal end of the suture needle. To secure the suture material 56 to the suture needle 54, the end of the suture material is simply forced into the recess 60 until the end of the recess is reached; and, thereafter, the suture material is pulled rearwardly or away from the suture needle causing the whisker-like filaments 64 to pass through the holes 62 providing a secure attachment. As shown in FIG. 7, the whisker-like filaments 64 may extend beyond the outer surface of the suture needle; however, the whiskers are angled proximally away from the sharp tip at the distal end of the suture needle thereby not interfering with smooth suturing Of course, the filaments 64 can have a length less than the length of the holes 62 so as not to extend externally of the suture needle. The suture device 52 is used in a similar fashion as the suture device 30.

The bore or recess 60 can extend along the length of the suture needle 54 as shown at 61 in dashed lines to form a lumen or chamber such that various local and/or systematic drugs can be stored in the lumens to be dispensed via the holes to the suture site. Such drugs include, for example, insulin, antitumor agents, antibiotics, contraceptive agents and the like. That is, by making the suture needles hollow with holes extending through the walls communicating with the lumen or chamber, drugs can be efficaciously applied to the suture site during suturing, and the lumen or chamber can be filled with a drug to be dispensed via the opening in the proximal end 58 and sealed in the suture needle by attachment of the suture material which does not extend the length of the lumen.

Another embodiment of a suture device according to the present invention is illustrated in FIG. 8 wherein a suture device 66 is formed of a suture needle 68 made of bioabsorbable material to have a desired rigidity therealong as described above and having any desired curved or straight configuration commonly used for suture needles with an eye 70 formed in a proximal end 72 thereof. A length of suture material 74, preferably made of flexible, elastic or stretchable bioabsorbable material, is attached to the suture needle 68 by passing the suture material through the eye 70, folding it back upon itself, slipping a ring or ring-like member 76, preferably made of bioabsorbable material, over the adjacent lengths of the suture material and securing the ends of the lengths of suture material together at an enlarged proximal end member 77, for example, by fusing or welding. The enlarged proximal end member 77 has a tapered locking neck 78 extending distally therefrom with protrusions thereon, such as proximally angled barbs, such that the locking neck can be received in the ring 76 in locking engagement.

In use, suturing is accomplished with the suture needle 68 in normal fashion with a double filament of the suture material pulled through the tissue, as shown in FIG. 9; and, the suture needle 68 is passed through a contractible loop or passage 79 defined by the adjacent lengths of suture material, the ring 76 and the enlarged proximal end member 77. Accordingly, the suture material 74 can be pulled tight until the ring 76 and the stretchable suture material proximal end member 77 abut the tissue with the desired tension, the neck 78 passing through the ring to lock the suture material in place and function similar to a conventional suture knot. After the suture material has been clamped between the proximal end member 77 and the ring 76 by the locking interaction therebetween, the suture material can be severed as shown at the dashed line C and the suture needle removed or the suture needle can be lodged in the tissue. If desired, an opening can be formed in the proximal end 72 of the suture needle to allow insertion of the length of suture material therein, and the suture material can be twisted to assure attachment of the suture material to the suture needle.

Another embodiment of a suture device according to the present invention is illustrated in FIGS. 10 and 11 wherein a suture device 80 is formed of a suture needle 81 made of bioabsorbable material to have a desired rigidity therealong as described above and having any desired curved or straight configuration commonly used for suture needles, the suture needle having a proximal end 82 formed with an arcuate channel 83 therein, circular in cross-section, extending from a side entrance 84 to an end position 86 aligned with the longitudinal axis of the suture needle A mouth 88 communicates with the channel 83 to receive a reduced diameter projection 89 at the distal end of a length of suture material 90, preferably made of flexible, elastic or stretchable bioabsorbable material. A ball 92 is formed on the end of projection 89, and the length of suture material has a proximal end 94 formed of an elastic loop 96 that can be stretched open, as shown in dash lines to define a passage 98 therethrough. The suture material 90 is attached to the suture needle 81 by inserting the ball 92 in the enlarged opening of entrance 84 and moving the ball along channel 83 to the end position 86, the projection 89 passing through mouth 88. The suture device 80 is used in a manner similar to that described above with respect to suture device 66 in that, after the suture needle penetrates the tissue to pull the suture material through the tissue, suture needle 81 is passed through the passage 98 in the proximal end which stretches to accommodate the largest transverse dimension of the suture needle and, thus, acts like loop 79 allowing the suture material to be pulled tight until the proximal end abuts the tissue with desired tension on the suture material. That is, the loop 96 contracts to clamp the length of suture material in the manner of a conventional suture knot, and the suture needle 81 can either be removed or lodged in the tissue.

Various bioabsorbable or biodegradable materials can be used to make the suture devices of the present invention with the composition determined by the rigidity or flexibility required. Generally, the bioabsorbable materials are thermoplastic polymers such as absorbable polymers and copolymers of poly-dioxanne, lactide, glycolide and the like. Polyglycolic acid is disclosed in U.S. Pat. Nos. 3,463,158; 3,739,773 and 3,772,420. Suitable polylactic acids are disclosed in U.S. Pat. No. 3,636,956. Examples of absorbable polyesters are shown in U.S. Pat. Nos. 3,225,766 and 3,883,901. Absorbable cellulose glycolic acid ethers are shown in U.S. Pat. No. 2,764,159. Examples of suitable esters of alpha-cyanoacrylic acid are found in U.S. Pat. Nos. 3,527,841, 3,564,078 and 3,759,264. The variable rigidity of the suture needles can be obtained by changing the bioabsorbable material composition in portions of the suture needles or by coating portions of the suture needles with bioabsorbable materials such as polycaprilactone.

The suture devices of the present invention can be any size from micro to macro dependent upon the surgical procedures for which they are designed for use; and, it should be appreciated that, while the suture devices of the present invention are particularly designed for use in endoscopic or closed procedures, they can also be used in open procedures since the time required for suturing is substantially reduced resulting in a significant reduction in overall operating time. The suture needles can taper throughout their length to a sharp tip or can have a constant diameter or cross section along their length with a sharp conical, pyramidal or polygonal tip at the distal end. The configuration of the suture needles in cross section can be varied in accordance with surgical procedures to be performed including, for example, circular, semi-circular, oval, lunar, rectangular, hexagonal, and polygonal solid or hollow configurations. Additionally, the outer surfaces of the suture needles can be grooved to facilitate penetration. The suture needles can be made in any conventional manner of working with plastic materials including molding, extrusion, stamping or cutting, and the suture needles and suture materials can be formed simultaneously or separately.

The lengths of suture materials can be made of conventional non-bioabsorbable materials or of bioabsorbable materials and can be elastic or stretchable for specific surgical procedures. As shown in FIGS. 5 and 8, multiple lengths of suture materials can be attached to the suture materials for specific surgical procedures and to effect a knot tying function.

Inasmuch as the present invention is subject to many variations, modifications and changes in detail, the above description of the preferred embodiments is intended to be exemplary only and not limiting.

What is claimed:

1. A method of suturing bodily tissue during endoscopic surgery comprising the steps of
    suturing the bodily tissue with a suture needle made of bioabsorbable material and a length of suture material attached thereto; and
    leaving the suture needle in the body to be absorbed thereby.

2. A method of suturing bodily tissue as recited in claim 1 and further comprising, after said suturing step, the step of separating the suture needle from the length of suture material.

* * * * *